(12) United States Patent
Alonso et al.

(10) Patent No.: US 6,645,723 B2
(45) Date of Patent: *Nov. 11, 2003

(54) METHOD FOR DETERMINING CYTOKINE RECEPTOR ACTIVATION BY THE USE OF AN ANTIBODY

(75) Inventors: Carlos Martinez Alonso, Madrid (ES); José Mario Mellado Garcia, Madrid (ES); Leonor Kremer Baron, Madrid (ES); José Miguel Rodriguez Frade, Madrid (ES)

(73) Assignees: Consejos Superior de Investigaciones Cientificas, Madrid (ES); Pharmacia Spain S.A., Barcelona (ES)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 22 days.

(21) Appl. No.: 09/044,154

(22) Filed: Mar. 19, 1998

(65) Prior Publication Data

US 2003/0077663 A1 Apr. 24, 2003

Related U.S. Application Data

(60) Provisional application No. 60/049,360, filed on Jun. 11, 1997.

(30) Foreign Application Priority Data

Mar. 19, 1997 (SE) ............................ 9701010-2

(51) Int. Cl.[7] ............................... G01N 33/53
(52) U.S. Cl. ................ 435/7.1; 435/7.2; 435/7.21; 436/547; 436/548; 530/388.1; 530/387.1
(58) Field of Search ................ 435/7.1, 7.2, 7.21; 530/387.1, 388.1; 436/547, 548

(56) References Cited

U.S. PATENT DOCUMENTS

| | | | | |
|---|---|---|---|---|
| 5,470,952 A | | 11/1995 | Stahl et al. | 530/350 |
| 5,506,107 A | | 4/1996 | Cunningham et al. | 435/7.21 |
| 5,593,844 A | | 1/1997 | Carlsson et al. | 435/7.1 |
| 5,599,681 A | * | 2/1997 | Epstein | 435/7.23 |

OTHER PUBLICATIONS

Sliwkowski, The Journal of Biological Chemistry 269(20): 14661–5 May, 1994.*

Baumgartner et al., "The Role of the WSXWS Equivalent Motif in Growth Hormone Receptor Function", *The Journal of Biological Chemistry*, vol. 269, No. 46, Nov. 18, 1994, pp. 29094–29101.

Lobie et al, "The Nuclear Growth Hormone Receptor Binding Protein", *The Journal of Biological Chemistry*, vol. 266, No. 33, Nov. 25, 1991, pp. 22645–22652.

Wells, "Binding in the Growth Hormone Receptor Complex", *Proc. Natl. Acad. Sci. USA*, vol. 93, Jan. 1996, pp, 1–6.

Abstract: Beattie et al, "An Immobilized Peptide Array Identifies Antibodies to a Discontinuous Epitope in the Extracellular Domain of the Bovine Growth–Hormone Receptor", *European Journal of Biochemistry*, vol. 239, No. 2, Jul. 15, 1996, pp. 479–486.

Gobius et al., "The First Disulphide Loop of the Rabbit Growth Hormone Receptor is Required for Binding to the Hormone", *Journal of Molecular Endocrinology*, vol. 9, 1992, pp. 213–220.

Mellado et al, "Conformational Changes Required in the Human Growth Hormone Receptor for Growth Hormone Signaling", *The Journal of Biological Chemistry*, vol. 272, No. 14, Apr. 4, 1997, pp, 9189–9196.

Bass et al, "A Systematic Mutational Analysis of Hormone–Binding Determinants in the Human Growth Hormone Receptor", *Proc. Natl. Acad. Sci. USA*, vol. 88, May 1991, pp. 4498–4502.

* cited by examiner

*Primary Examiner*—Lorraine Spector
(74) *Attorney, Agent, or Firm*—Dinsmore & Shohl LLP (57) ABSTRACT

The present invention relates to a method for determinating cytokine receptor, especially growth hormone receptor (GHR), activation, by the use of an antibody capable of discriminating between an activated and an inactive cytokine receptor conformation, especially GHR or growth hormone binding protein (GHBP) conformation, the method comprising: contacting the antibody and the cytokine receptor to form a complex, contacting a candidate ligand to the complex, measuring the antibody binding to inactive cytokine receptor and thereby discriminating between an activated and an inactive conformation. The invention also relates to an antibody directed to the hinge spanning subdomains I and II of the growth hormone receptor extracellular region and which is capable of discriminating between an activated and an inactive receptor conformation. The invention also relates to the use of the antibody for e.g. characterization of growth hormone receptor interactions and for screening for compounds stabilising die dimerization of GHR.

20 Claims, 9 Drawing Sheets

METHOD FOR DETERMINING CYTOKINE RECEPTOR ACTIVATION BY THE USE OF AN ANTIBODY

This application claims benefit of provisional application Ser. No. 60/049,360 filed Jun. 11, 1997.

The present invention relates to a method for determining cytokine receptor, especially growth hormone receptor (GHR), activation, by the use of an antibody capable of discriminating between an activated and an inactive cytokine receptor conformation, especially GHR or growth hormone binding protein (GHBP) conformation, the method comprising: contacting the antibody and the cytokine receptor to form a complex, contacting a candidate ligand to the complex, measuring the antibody binding to inactive cytokine receptor and thereby discriminating between an activated and an inactive conformation.

It also relates to a method for screening for a functionally cytokine agonists and antagonists, especially functionally growth hormone (GH) agonists, among candidate ligands by the use of an antibody specific for activated cytokine receptor conformation. The invention also relates to an antibody directed to the hinge sparing subdomains I and II of the growth hormone receptor extracellular region and which is capable of discriminating between an activated and an inactive receptor conformation.

The invention also relates to the use of the antibody for e.g. characterization of growth hormone receptor interactions and for screening for compounds stabilizing the dimerization of GHR.

INTRODUCTION

The 22 kDa polypeptide human growth hormone (hGH), essential for normal growth and development, induces a variety or biological effects including linear growth, lactation, nitrogen retention, diabetogenic and insulin-like effects and macrophage activation (1–4). Each of these effects is initiated by hGH interaction with specific cell receptors. The hGH receptor (hGHR) belongs to a large cytokine receptor family (5) which includes receptors for prolactin, erythropoietin, interleukins (IL)-2, 4, and -6, granulocyte macrophage-colony-stimulating factor (GM-CSF) and granulocyte-colony-stimulating factor (G-CSF) (6–10). The three-domain organization of these receptors comprises a heavily N-glycosylated extracellular ligand binding domain, a single transmembrane segment and an intercellular domain, the last of which shares little sequence identity within the family (11). The hGHR extracellular region has two subdomains, one implicated mainly in hGH binding (subdomain I) and the other in hGHR dimerization (subdomain II) (7, 8).

The extracellular hGHR domain is found in serum in the form of a hormone binding protein (hGHBP) which binds hGH with approximately the same affinity and specificity as the intact receptor (12). Non-glycosylated recombinant bacterial hGHBP (13) has the same binding affinity ($K_d$=0.4 nM) (14) and specificity for hGH as the mammalian binding protein. Crystallization studies of hGH and hGHBP show that a single hGH molecule binds two hGHBP molecules (15). Each hGH molecule is bivalent, containing two separate hGHBP binding sites; site I is a high affinity site and site II, a low affinity site. In contrast, the hGHBP is univalent, as it uses the same amino acids to bind either hGH site I or site II. An hGH excess dissociates the hGH-(hGHBP)$_2$ complex to form a monomeric complex. Biological response triggering requires sequential binding of the first receptor subunit to site I on a GH molecule, followed by binding of the second receptor to GH site II, forming the GH-(GHR)$_2$ complex (16). In addition to the hormone-receptor interactions, there is also substantial surface contact between the subdomain II subunits of the extracellular regions of the two receptor molecules. This sequential dimerization model has been confirmed using several approaches including crystallization, size exclusion chromatography, calorimetry and fluorescence quenching assays (14).

Although little is known of the hGHR signal transduction mechanism, several lines of evidence indicate that hGHR activation triggers tyrosine phosphorylation of JAK2 kinase (17) and some STAT transcription factors, mainly STAT2, STAT3 and STAT5 (18–21).

Earlier methods for determining whether a candidate ligand is an agonist or an antagonist to a growth hormone receptor, has been based on the theory that it must be determining whether the ligand forms a complex of one or two growth hormone receptors. See WO 92/21029.

However, Hardinger et al in J Biol Chem, 1996, Vol 271 (12) 6708–12, have found that both native hGH and hGH-G120R form complexes similar in size to that expected for hGH when bound to recombinant hGH binding protein. They further conclude. "our results indicates that the GH antagonist, hGH-G120R, is able to bind, dimerize, and internalize GHRs in a similar manner as hGH. However, the dimeric complex formed with hGH-G120R is not functional as in the hGH:GHR dimer.

We present here the novel finding that the measurement of a conformation change of the GH receptor is the relevant measurement for the determination whether a ligand is an agonist or an antagonist to the growth hormone receptor.

ABBREVIATIONS USED

| | |
|---|---|
| EDC/NHS | N-ethyl-N'-(3-dimethylaminopropyl) carbodiimidehydrochloride/ N-hydroxysuccinimide) |
| EIA | enzyme-linked immunoassay |
| FCS | fetal calf serum |
| GAM-PO | goat anti-mouse immunoglobulin antibody |
| G-CSF | granulocyte colony-stimulating factor |
| GM-CSF | granulocyte macrophage-colony-stimulating factor |
| hGH | human growth hormone |
| hGHBP | human growth hormone binding protein |
| hGHR | human growth hormone receptor |
| IL-2, IL-4, IL-6 | interleukins 2, 4 and 6 |
| PBS | phosphate-buffered saline |
| PO | peroxidase |
| OPD | o-phenylenediamine dihydrochloride |
| RAM | rabbit anti-mouse |
| sc | subcutaneous |
| SDS-PAGE | sodium dodecyl sulphate polyacrylamide gel electrophoresis |

THE INVENTION

We have developed a panel of human growth hormone receptor-specific monoclonal antibodies (mAb), used for the characterization of signals triggered by hGH binding. One of these was used here to characterize hormone/receptor interactions. This antibody, GHR05, is directed against the hinge spanning subdomains I and II of the receptor's extracellular region and recognizes uncomplexed hGHR on the cell surface. Binding assays indicate a higher affinity of GHR05 for the hGH-hGHR complex than for hGHR alone, indicating that the mAb better recognizes a receptor conformation induced following ligand binding. Antibody binding to the cell surface receptor increases upon receptor binding to growth hormone, but not when it binds a mutant form, hGHG120R, which does not trigger receptor activation. Growth hormone binding thus appears to lead to a conformational change in the receptor epitope recognized by GHR05, giving rise to the active dimer configuration, necessary for signal transduction. The antibody appears thus to activate the cells through conformational changes, which are different from those triggered by GH.

Binding assays indicate a higher affinity of GHR05 for the hGH-hGHR complex than for hGHR alone, indicating that the mAb better recognizes a receptor conformation induced following ligand binding.

Using a chimeric receptor-expressing, growth hormone-dependent murine cell line, we find that GHR05 binds to the receptor in the absence of hGH and delivers a signal leading to cell proliferation, i.e. activation. Finally, GHR05 treatment of IM-9 cells, a human cell line expressing a functional hGHR, leads to cell proliferation mediated by the generation of GH-specific signals, including phosphorylation of the JAK2 tyrosine kinase and activation of STAT5.

The invention is defined according to the attached claims.

The invention also includes screening against the monomer for prevention of the dissociation of the already-formed complex and blocking the activity of the preformed complexes.

The binding of the claimed antibody to GHR or to GHBP is not inhibited by soluble GH and the antibody has an ability to recognize the GHR and the GHBP in western blot The antibody has also an ability to recognize in flow cytometry, all cells naturally expressing the GHR or cells transfected with a plasmid containing the gene that encodes the GHR. Another ability is to immunoprecipitate the BP-GH-1125-complex.

The screening of compounds with properties similar to GHR05 is possible by this invention.

GHR19, an isotype-matched hGHR-specific mAb was developed, which recognizes the monomer and triggers apoptosis.

To analyze the consequences of hGHR/hGH interaction, we tested the effect of GHR05 on hGHR-expressing IM-9 cells and on the Ba/F3 (8/6) cell line. These latter cells were generated from the IL-3-dependent murine pro-B cell line Ba/F3 (22) transfected with a chimeric gene containing the hGHR extracytoplasmic domain and the hG-CSFR intacytoplasmic domain; they require either IL-3 or hGH for in vitro growth. Following its binding to the receptor and in the absence of hormone or cytokines, GHR05 triggers a signal leading to bcl-2 expression and cell growth in Ba/F3 (8/6) cells. Both GHR05 and hGH promote IM-9 cell proliferation and activate the JAK/STAT pathway. A model is proposed in which the first step in GH-mediated cell proliferation is associated with a conformational change in the growth hormone receptor structure.

EXPERIMENTAL PROCEDURES

Proteins, antibodies and cell lines. Recombinant human GH 22K (rhGH-22K, Genotropin) and recombinant human GHBP were obtained from Pharmacia & Upjohn (Stockholm, Sweden). hGHG120R was kindly donated by Dr. Gunnar Norstedt (Center for Biotechnology, Karolinska Inst., Huddinge, Sweden). IM-9 cells were from the ATCC (Rockville, Md.). Ba/F3 (8/6) cells were generated by transfection of Ba/F3 cells with the chimeric construct hGHR/hG-CSFR and cultured in RPMI-1640 medium supplemented with IL-3 (10 U/ml) and 10% fetal calf serum (FCS) at 37° C. in 5% $CO_2$. Anti-human JAK2 mAb was from Upstate Biotechnology, Inc. (UBI, Lake Placid, N.Y.), anti-human STAT5, anti-murine c-myc and anti-murine bax mAb were from Santa Cruz Biotechnology, Inc. (Santa Cruz, Calif.), anti-murine bcl-2 mAb was from Oncogene Science, Inc. (Cambridge, Mass.), and anti-murine p53 mAb was from Transduction Laboratories (Lexington, Ky.).

Preparation of monoclonal antibodies. BALB/c mice were immunized subcutaneously (s.c.) with 10 μg of GHBP in 0.1 ml sterile phosphate-buffered saline (PBS) and Freund's complete adjuvant (Difco, Detroit, Mich.). They were boosted s.c. on days 30 and 60 with 10 μg of protein in Freund's incomplete adjuvant, and intraperitoneally in PBS on day 90. Mice were boosted intravenously with 10 μg of protein in PBS on days −3 and −2 before cell fusion. Mouse spleen and/or lymph node cells were fused with the P3X63-Ag8.653 mycloma cell line (CRL 1580, American Type Culture Collection, Rockville, Md.) using polyethylene glycol 4000 (Merck, Darmstadt Germany) following standard protocols (23, 24). Supernatants were tested for antibodies using an enzyme-linked immunoassay (EIA) and positive hybridomas were cloned. Hybridomas were cultured in RPMI-1640, 10% FCS at 37° C. in 5% $CO_2$. Monoclonal antibodies were produced in tissue culture supernatants and murine ascites fluids (25) and purified by $(NH_4)_2SO_4$ precipitation (24). Antibody isotypes were determined in EIA using peroxidase (PO)-labeled subclass-specific anitisera (ICN, Irvine, Calif.).

Protein biotinylation. Proteins were biotinylated as described (26). GHBP and mAb (0.5 mg in 0.5 ml of 150 mM NaCl, 0.1 M carbonate buffer, pH 9) were incubated with 50 μl of 1 mg/ml N-hydroxysuccinimide biotin in dimethylsulphoxide (Sigma, St. Louis, Mo.) for 120 min at room temperature. Free biotin was removed by dialysis agant PBS. Biotin-labeled protein was diluted 1:2 with glycerol and stored at −20° C.

Enzyme-linked immunoassays. Four different enzyme-linked-immunoassays (EIA) were performed that varied in their mechanism of antigen presentation to the antibody.

1. Antibody capture assay. Biotin-labeled GHBP (0.5 μg/ml in PBS, 100 μl/well) were adsorbed to avidin-coated microtiter plates (3 μg/ml) (Maxi-sorb, Nunc, Copenhagen, Demark) for 90 min at 37° C. Remaining protein-binding sites were blocked with 0.5% BSA in PBS. Plates were washed with distilled water and mAb incubated for 60 min at 37° C., followed by a PO-labeled goat anti-mouse immunoglobulin antibody (GAM-PO; Tago, Burlingame, Calif.) and o-phenylenediamine dihydrochloride (OPD, 4 mg/ml in 0.15 M sodium citrate buffer, pH 5.0; Sigma). The reaction was terminated with 3N sulpburic acid and optical density determined at 492 nm.

2. Antigen capture assay. Monoclonal antibodies were adsorbed to the solid phase, directly (3 µg/ml in PBS) or via an affinity-purified GAM antibody. After blocking, biotin-labeled GHBP (1/1000) in PBS-0.5% BSA was incubated for 60 min at 37° C., followed by PO-labeled streptavidin (Sigma) for 30 min at 37° C., and OPD. The reaction was terminated as above.

3. Sandwich capture assay. Purified mAb (3 µg/l in PBS) was adsorbed to microtiter plates. After overnight incubation at 4° C. and blocking with 0.5% BSA, GHBP dilutions in PBS-0.5% BSA were added and incubated for 60 min at 37° C. After washing, a biotin-labeled second mAb was added, followed by PO-streptavidin and OPD. The reaction was terminated as before.

4. Competitive assay. GHBP (1 µg/ml in PBS) was adsorbed to microtiter plates overnight at 40° C., the blocked with PBS-0.5% BSA for 60 min at 37° C. Plates were washed, and biotinylated mAb, alone or mixed with competitor antibodies, was added and incubated for 90 min at 37° C., followed by PO-streptavidin. The reaction was terminated as above. Competition for GHBP binding was assumed when a signal decrease of more than 40% was observed in the presence of the added antibody compared to that of GHR05 alone; that is, the two mAb recognized similar or proximal epitopes on the GHBP molecule.

Determination of kinetic parameters using real-time interaction analysis. BIAcore real-time interaction analysis (Pharmacia, Uppsala, Sweden) was used to determine the kinetic parameters of mAb binding to hGHBP and the hGH-hGHBP complex. The carboxylated dextran CM-5 matrix of a sensor chip was activated with an EDC/NHS (N-ethyl-N'-(3-dimethylaminopropyl) carbodiimidehydrochloride/ N-hydroxysuccinimide) mixture (Pharmacia). Rabbit anti-mouse immunoglobulin light chain (35 µl at 50 µg/ml, Pharmacia) solubilized in 10 mM acetate buffer, pH 4.5, was then immobilized on the matrix via primary amine groups in 10 mM Hepes, 150 mM NaCl, 3.4 mM EDTA, 0.05% surfactant P20, pH 7.4 (HBS) at a flow rate of 5 µl/min. Unreacted groups were blocked with 35 µl ethanolamine-HCl, pH 8.5. Determinations were performed at 25° C. using eight GHBP concentrations (4–500 nM), alone or complexed with a 20X molar excess of hGH. GHBP or GH/GHBP were injected in HBS at a constant 5 µl/min flow rate over the GHR05 mAb, previously captured by dextran-immobilized rabbit anti-mouse light chains. After each determination, the surface was regenerated for 3 min with 30 mM HCl. Kinetic rate constants ($k_{on}$, $k_{off}$) and the apparent equilibrium affinity constants ($K_a = k_{on}/k_{off}$) were determined using BIAlogue Kinetics Evaluation Software (Pharmacia).

Cytofluorimetric analysis. Cells ($2 \times 10^5/100$ µl) were plated in V-bottom 96-well plates and incubated with 100 µl of 70% ethanol for 10 min at 40° C. for permeabilization, or in PBS with 2% BSA and 2% FCS ($PBS_{st}$). After washing with $PBS_{st}$, cells were incubated with 1 µg/ml hGH or $PBS_{st}$ for 30 min at 4° C., washed twice and incubated with 100 µl of undiluted supernatants for 30 min at 4° C. Cells were washed twice with $PBS_{st}$, fluorescein isothiocyanate labeled-GAM (GAM-FITC, Southern Biotechnologies, Birmingham, Ala.) was added and incubated for 30 min at 4° C. Samples were analyzed in an EPICS XL flow cytometer (Coulter Electronics Inc., Hialeah, Fla.).

Immunoprecipitation, SDS-PAGE and Western blots analysis. Hormone or antibody-treated cells ($2 \times 10^6$) were lysed in 50 mM Tris-HCl pH 7.6, 1% Nonidet P40, 250 mM NaCl, 0.5 mM EDTA, 10 mM NaF, 10 mM Na pyrophosphate with protease inhibitors for 20 min at 4° C. and centifuged at 15,000×g. Protein extracts were separated in 12.5% sodium dodecyl sulphate polyacrylamide gel electrophoresis (SDS-PAGE) and transferred to nitrocellulose membranes. For western blot analysis, membranes were blocked with 5% non-fat dry milk in 20 mM Tris-HCl pH 7.5, 150 mM NaCl (TBS) and incubated overnight at 4° C. with primary antibody in TBS-5% non-fat dry milk. Membranes were washed with 0.1% Tween-20 in TBS-0.5% non-fat dry milk and incubated with PO-labeled second antibody. After wasting, labeled proteins were developed using the ECL system (Amersham, Little Chalfont, UK). When stripping was required, membranes were incubated with 62.5 mM Tris-HCl pH 6.8, 2% SDS, 0.1 M 2-mercaptoethanol for 90 min at 60° C. and washed extensively with TBS before reblocking and probing.

Immunoprecipitation was performed as described (27). Briefly, protein extracts were pre-cleared by incubation with 20 µg of anti-mouse IgG-agarose (Sigma) for 60 min at 4° C. and centrifugation for 1 min at 15,000×g. Phosphotyrosine-containing proteins were imunoprecipitated with anti-phosphotyrosine mAb (5 µg/sample) (Transduction Laboratories) for 90 min at 4° C., followed by anti-mouse lgG-agarose. Samples were centrifuged, the agarose pellets washed twice in detergent buffer and three times in 50 mM Tris-HCl pH 7.6, resuspended in Laemmli buffer and proteins resolved by electrophoresis.

Cell proliferation assay. Ba/F3 (8/6) cells ($20 \times 10^5$/ml) were washed in basal RPMI 1640 medium without IL-3. Then, 25 µl of the cell suspension were added to 96-well plates and treated with hGH (0.001 nM-10 nM) or mAb in a final volume of 100 µl for 18 h at 37° C. Confluent IM-9 cells ($1 \times 10^6$/ml) were washed in serum-free RPMI 1640 and 100 µl of the cell suspension were incubated in 96-well plates in the presence of hGH or mAb for 8 h at 37° C. To measure DNA synthesis, 1 µCi/well of [$^3$H]thymidine (Amersham) was added (5 Ci/mmol), incubated 6 h at 37° C. in 5% $CO_2$. Cells were harvested, washed on glass fiber filters and [$^3$H]thymidine uptake quantified by liquid scintillation counting.

Cell cycle analysis. Cell cycle stage was assessed by cell DNA content using propidium iodide staining and flow cytometry analysis. Briefly, subconfluent cells were washed three times in RPMI-10% FCS without IL-3 (basal medium), plated at $3 \times 10^5$ cells/well in 24-well plates (Nunc) and treated with hGH (10 µg/ml) or mAb (1 µg/ml), to a final volume of 1 ml. After 24 h incubation at 37° C. in 5% $CO_2$, cells were centrifuged 10 min at 200×g and resuspended in 100 µl of PBS. Cell were permeabilized and DNA stained by adding 100 µl) detergent followed by 1.2 ml propidium iodide solution (Coulter DNA-Prep® reagents). After vortexing, samples were incubated at 37° C. for 30 min and analyzed in an EPICS-XL cytometer (Coulter).

RESULTS

Figure 1A:
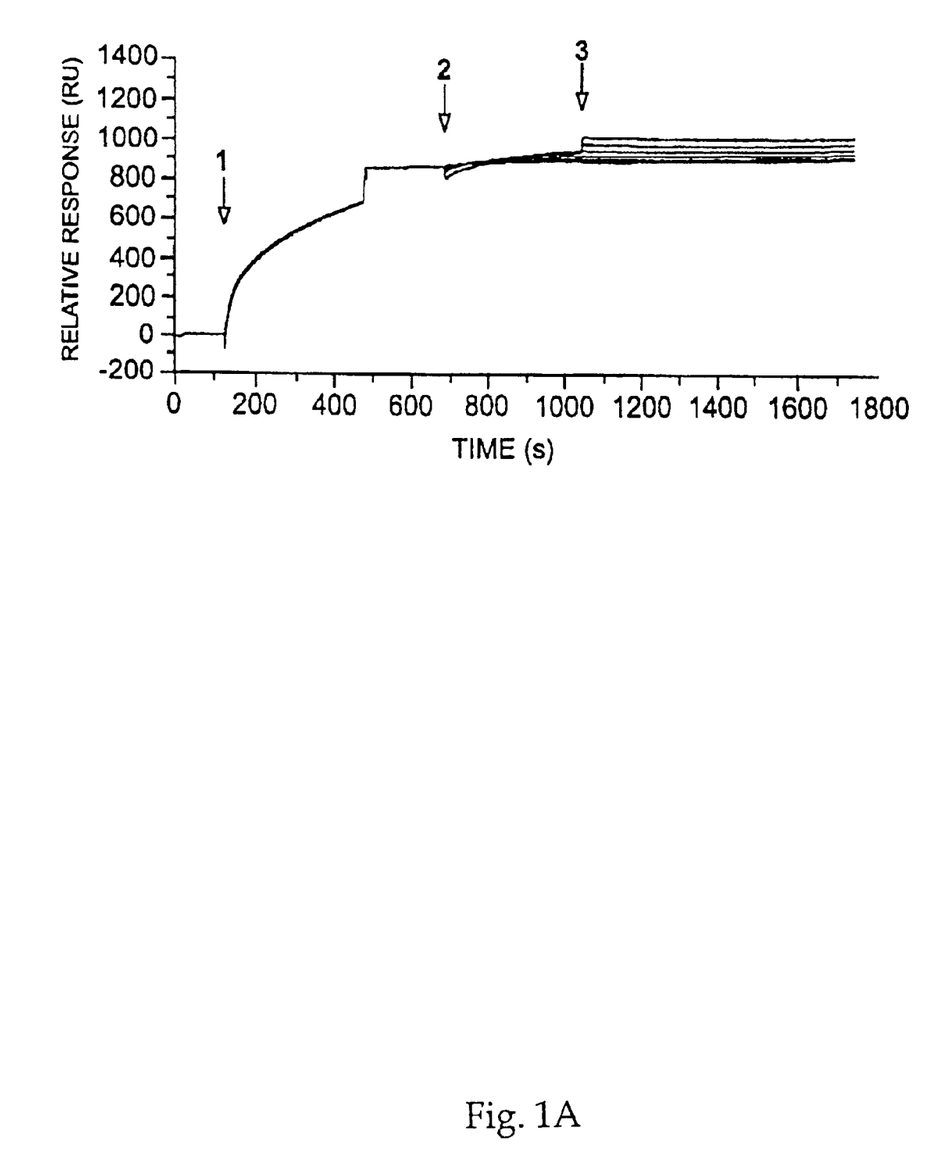
FIGS. 1A–C Principal characteristics of the GHR05 mAb.
Figure 1B:
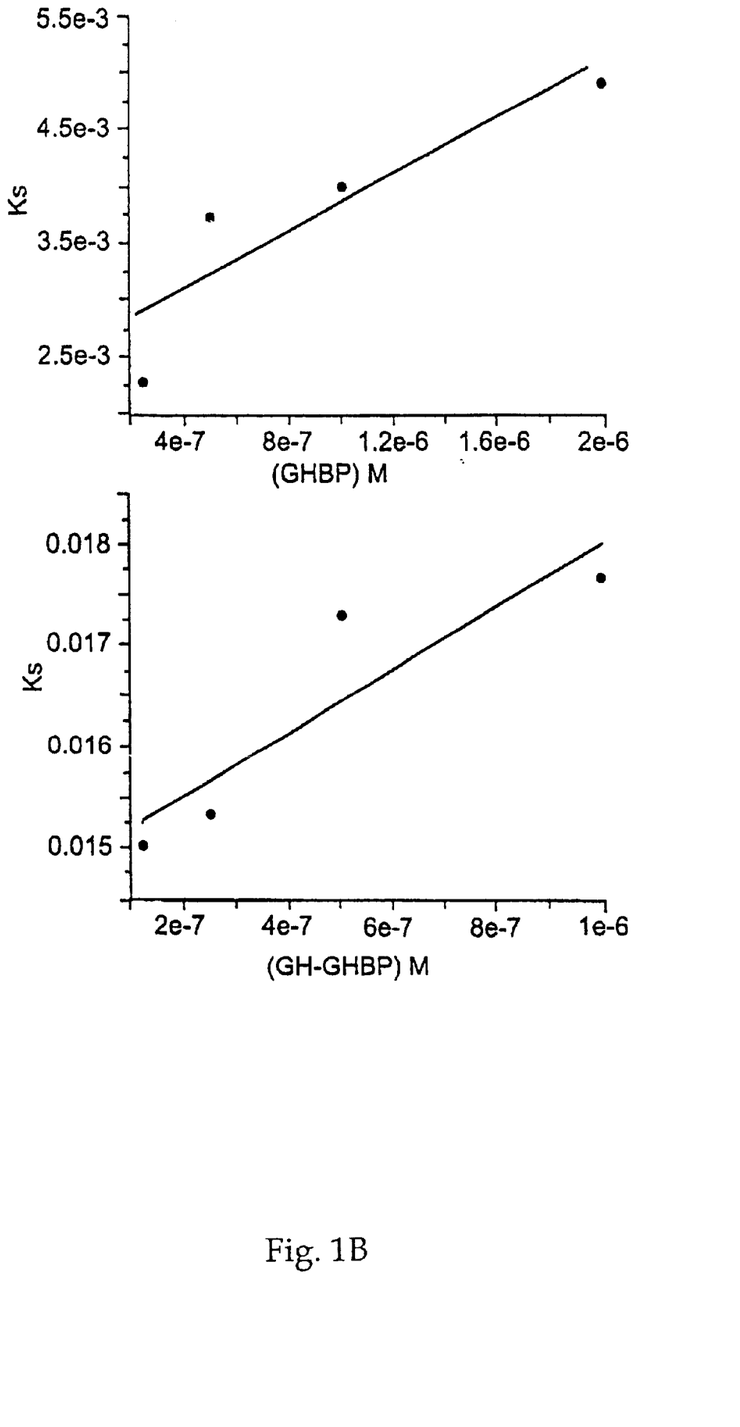

Characterization of anti-growth hormone receptor antibody. Using *E. coli*-derived recombinant hGHBP as immunogen, we generated a series of mAbs, one of which (GHR05) was further characterized. GHR05 is an IgM, k antibody specific for the hGH receptor, with a $K_a$ of 2.5 or $6 \times 10^6$ M$^{-1}$ as measured in BIAcore using GHBP or GH/GHBP complex, respectively. The BIAcore measures real-time interactions and thus determines the association of GH05 to GHBP or GH/GHBP with no appreciable differences ($1.7 \times 10^3$ and $3.2 \times 10^3$ M$^{-1}$s$^{-1}$, respectively) (FIGS. 1A, B). However, GHR05 dissociates less rapidly from GHBP ($2.6\times10^4$ s$^{-1}$) than it does from the GH/GHBP complex ($1.2\times10^{-3}$ s$^{-1}$). Thus, this antibody binds with similar $K_{on}$ to both GHBP and the complex, although the dissociation data indicate that the GHR05/GHBP complex is more stable than that of GHR05/GH/GHBP.

Figure 1C:
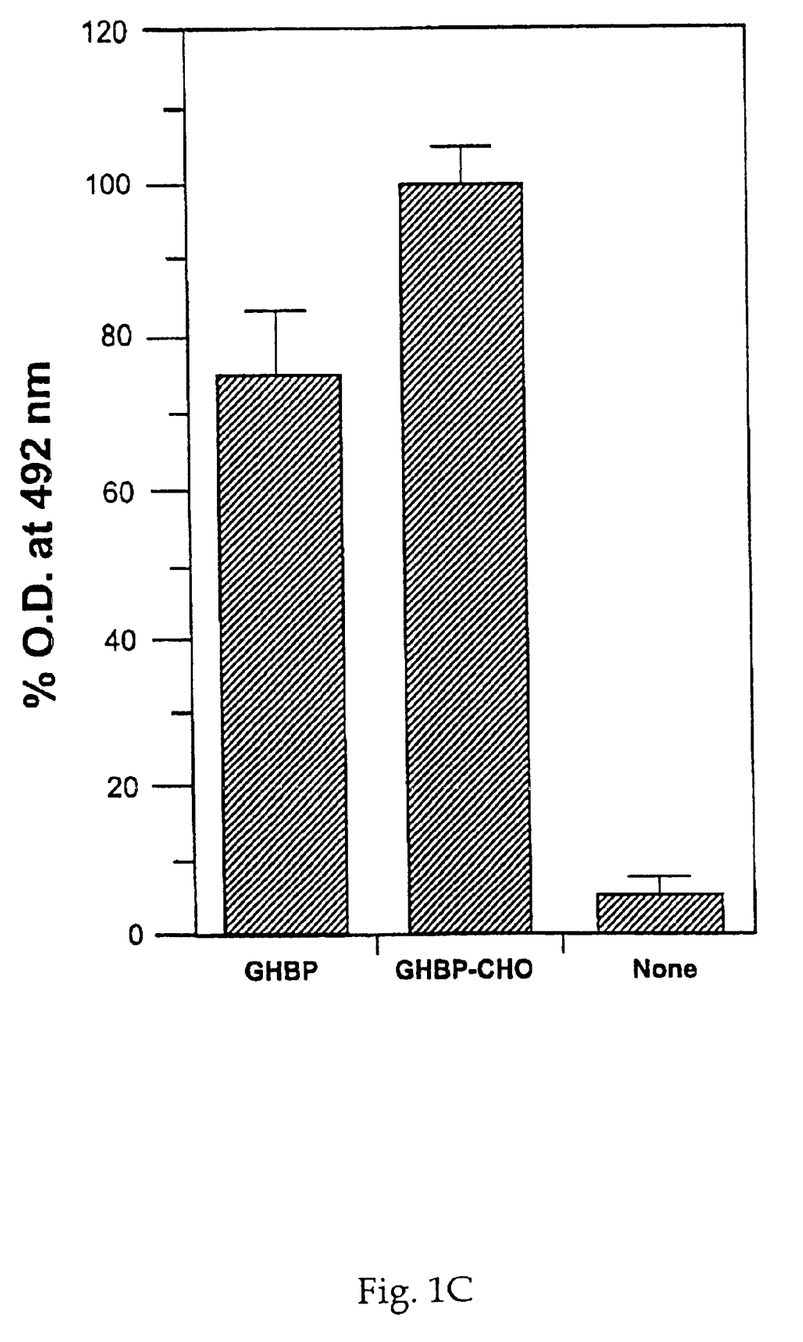

As one characteristic of cytokine receptors is their heavy glycosylation, and the ultimate use of GHR05 was the study of the GHR we tested its recognition of the CHO-derived GHBP. In antigen capture EIA, GHR05 recognizes GHBP, whether glycosylated or not (FIG. 1C). Recognition was also apparent in antibody capture EIA, western blot, immunoprecipitation and real-time specific interaction using GHR05 coupled to a dextran matrix or in liquid phase (not shown).

To determine the hGHR region recognized by GHR05, three different assays were designed, based on the ability of this mAb to bind simultaneously with or to compete for GHBP binding with other anti-GHR mAb that recognize sequential or conformational epitopes. These assays include a sandwich EIA, a competitive EIA and an additive assay in BIAcore. The data provide information on those mAbs that bind simultaneously to a single GHBP molecule, those that bind to overlapping or identical epitopes and, using hGH, those with interfering or non-interfering interactions with the ligand binding site. With these assays, the epitope recognized by GHR05 was determined to lie in the hinge between subdomains I and II of the extracellular receptor domain. This epitope does not form part of the hGH binding site.

Figure 2:
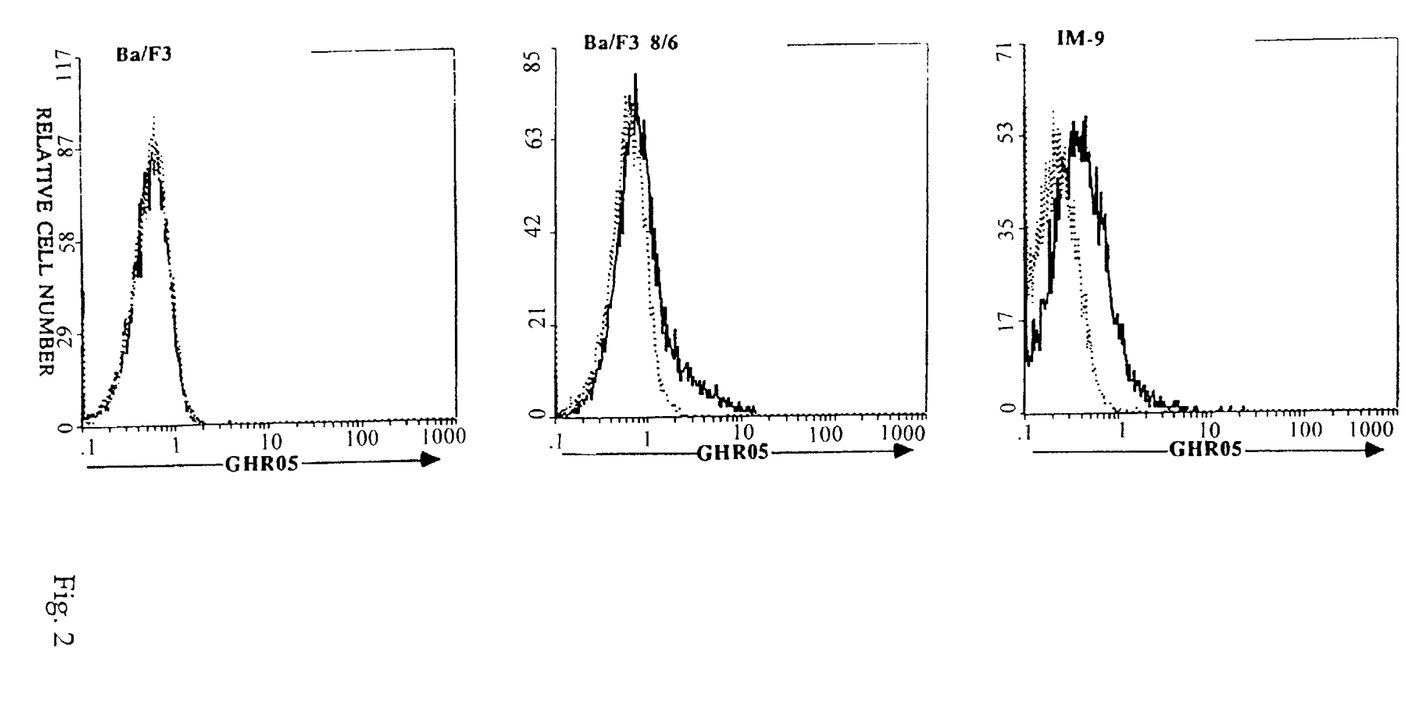
FIG. 2. GHR05 binding to different hGHR-expressing cell lines

We assessed GHR05 reactivity with the hGHR expressed on the surface of two different cell lines. We tested IM-9, a human B cell line which expresses a functional hGHR (28) as shown by its ability to respond to hGH by enhancing cell proliferation (29), IgG production (30) and $[Ca^{2+}]_i$ influx (31). We also used the IL-3-dependent murine pro-B cell line BW73 (22), transfected with a chimeric gene containing the hGHR extracytoplasmic domain and the intracytoplasmic domain of the human granulocyte colony-stimulating factor receptor (Bs/F3 (8/6)). Although both wild-type and transfected cells grow in the presence of exogenous IL-3, only transfected cells proliferate in the presence of hGH (32). GHR05 recognizes hGHR in both IM-9 and Ba/F3 (8/6) cell lines, as a significant fluorescence shift (15%) was observed in flow cytometry, while no binding was seen in non-transfected Ba/F3 cells (FIG. 2).

The GHR05 antibody recognizes an activating epitope on the growth hormone receptor. Dimerization of the hGHR appears essential for correct signal delivery. To evaluate the capacity of GHR05 to recognize the hGH-(hGHR)$_2$ dimer complex, binding of several mAbs to Ba/F3 (8/6) cells pretreated with saturating hGH concentrations ($0.45\times10^{-6}$M) was studied GHR05 binding to the complexed receptor increases, while the binding of other mAb is unaffected (mAb 263) or diminished (GHR25) (FIGS. 3A, B, C). These phenomena appear not to be due to stabilization of mAb binding to the hGH/hGHR, at least in terms of affinity, since BIAcore measurements show that GHR05 has similar apparent $K_a$ for both hGHBP and the hGH/hGHBP complex (FIGS. 1A, B).

GHR05 binding to hGHR increases dramatically when cells are previously is permeabilized (FIG. 3E). This phenomenon is GHR05-specific, as this mAb binds to 100% of cells following permeabilization, which is not the case for mAb specific for other hGHR domains (FIG. 3F). This increase cannot be described to hGH/hGHR complex internalization, since the experiment was performed in the absence of hGH, nor to the receptor glycosylation pattern, as glycosylation did not alter GHR05 recognition (FIG. 1C). Thus, the binding increase may be due to improved exposure of the GHR05 binding epitope.

To analyze the possible relationship between the GHR05 binding increase and hGH-induced receptor conformational change, an hGH mutant (hGHG120R) was employed that is able to bind the hGHR but not to form the active hGH-(hGHR)$_2$ complex. hGHG120R has a Gly$_{120}$>Arg mutation affecting the second GH binding site, which impedes correct receptor dimerization and subsequent proliferation induction (33). This molecule has been shown to act as a GH antagonist both in vitro (13, 16, 34) and in vivo (34). In contrast to hGH, the presence of hGHG120R does not modify GHR05 receptor binding (FIG. 3D), permitting us to conclude that GHR05 better recognizes an epitope which becomes exposed in the active, but not in the inactive, receptor complex. GHR05 signals through the hGHR and promotes cell proliferation. As shown earlier, GHR05 binds to hGHR-expressing cells in the absence of ligand. To study the biological significance of this binding, we studied cell cycle starts in hGH-dependant Ba/F3 (8/6) cells treated with hGH, GHR05 or GHR19, an isotype-matched hGHR-specific mAb. After 24 h, cell cycle distribution was analyzed by flow cytofluorometry. The hGH-treated cells were in subconfluent growth, while the GHR19-treated cells showed a marked increase in the sub-G$_1$ population, indicative of apoptosis. When cells were GHR05-treated, however, the apoptosis ratio was significantly lower than that of the GHR19-treated cells, while the ratio of proliferating cells increased (FIG. 4). This indicates that GHR05 binding induces a GH-like signal.

Figure 5:
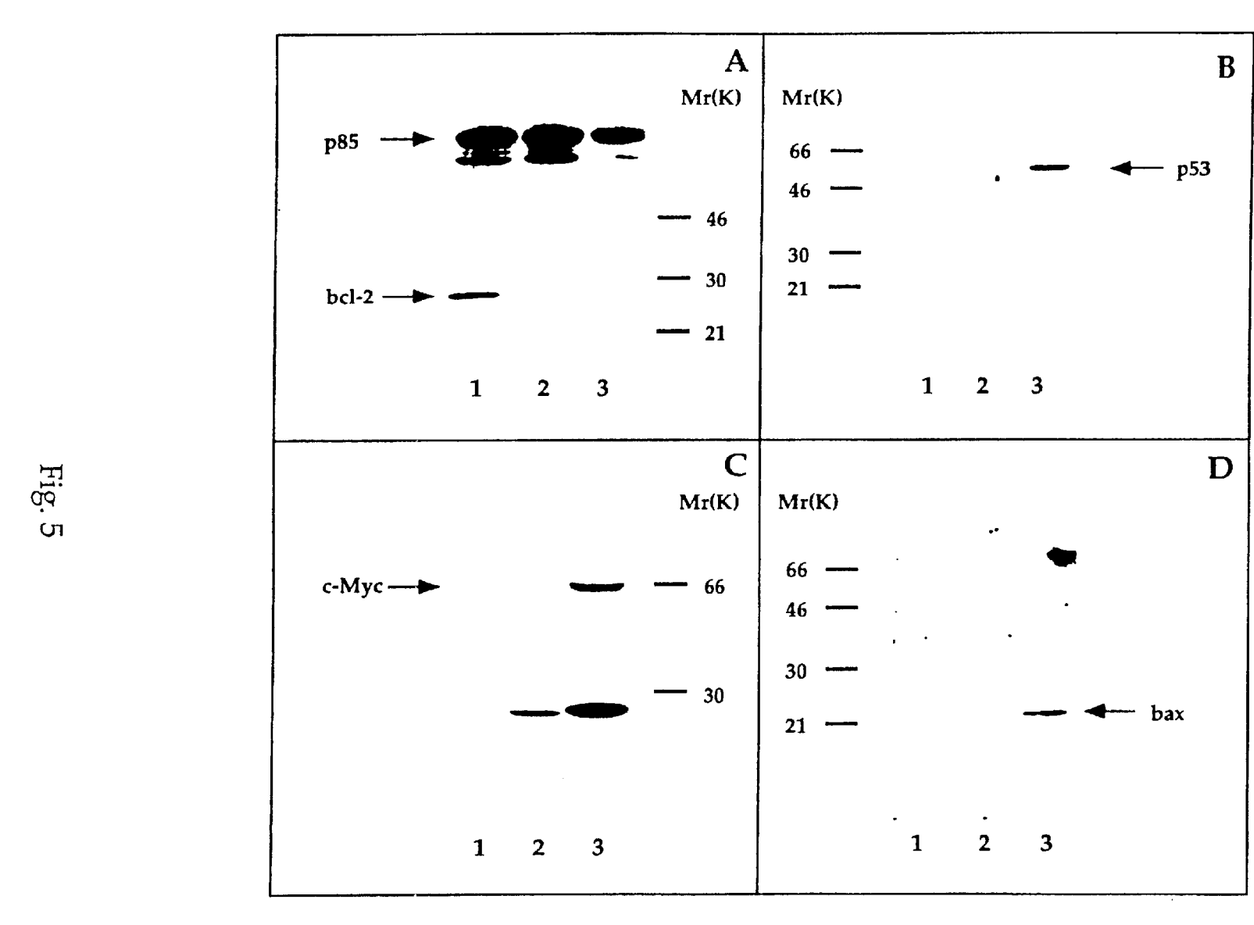
FIGS. 5A–D Expression of genes implicated in cell survival or death in hGH- or GHR05-treated Ba/F3 (8/6) cells.

The GHR05-triggered cell survival effect was further characterized by studying the expression of the cell survival control proteins bcl-2 (35), bax, p53, as well as of c-myc, whose deregulated expression drives certain cells into apoptosis following growth factor deprivation. hGH or GHR05 treatment of cells causes bcl-2 expression while preventing induction of bax, p53 and c-myc, which are expressed upon treatment with other anti-hGHR mAb (FIG. 5).

To further assess the proliferative effect induced by GHR05 binding, we measured hGH- and GHR05-promoted [$^3$H]thymidine incorporation into Ba/F3 (8/6) cells. GHR05 induces significantly greater cell proliferation (25%) than does a control mAb (8%, equivalent to background) (FIG. 6A). The maximum GHR05-induced [$^3$H]thymidine incorporation level is equivalent to that promoted by 4 pM hGH. Thus, GHR05 binding to the GHR promotes specific signals responsible for inducing cell growth. As the epitope recognized by GHR05 is modified when hGH is bound to the receptor, we tested whether antibody binding in the presence of hGH has a synergistic or an additive effect on cell proliferation. No differences in proliferation were observed when cells were incubated simultaneously with GHR05 and hGH (data not shown).

As Ba/F3 (8/6) are artificially generated GH-responsive cells, the results were validated using the human IM-9 cell line, which expresses the full-length hGHR. Both GHR05 and hGH promote IM-9 cell proliferation (FIG. 6B) To further verify GHR05 signaling specificity, IM-9 cells were treated with hGH and GHR05, and the thyrosine phosphorylation status of JAK2 and STAT5 determined. The same JAK2 and STAT5 expression pattern is observed with both treatments, indicating the agonistic behavior of GHR05 (FIG. 7). We therefore conclude that GHR05 triggers GH-like cell activation and proliferation following hGHR binding.

DISCUSSION

Using *E. coli*-derived rhGHBP as immunogen, we obtained the hGHR-specific mAb GHR05. Fine characterization of its reactivity using the soluble cellular region of the receptor (GHBP) and competitive binding with other anti-GHR mAb allow mapping of the epitope recognized by this mAb to the hinge region between GHR subdomains I (binding domain) and II (dimerization domain). This epitope is unrelated to sequences involved in GH binding to the receptor (15). These data correlate well with the fact that this mAb recognizes both GHBP and GHR complexed with GH. However, some interesting differences are apparent when the behavior of the mAb with GH/GHBP or with GH/GHR complexes is compared.

GHR05 binding to cell membrane hGHR increases following hGH activation, as determined by flow cytometry analysis using cells expressing either the native hGHR or a chimeric hGHR/hG-CSFR form. Its affinity for the soluble receptor form, GHBP, is similar to that for the GH/GHBP complex, indicating that the epitope recognized by GHR05 is not altered by GH binding in saturating conditions. When the association and dissociation constants are further analyzed, GHR05 binding to the GH/GHBP complex appears less stable than its binding to GHBP alone. Characteristics differ in each of these assays, as the continuous flow in BIAcore allows measurement of association and dissociation to a single GHBP molecule, while the measurement of binding to intact cells in flow cytometry permits equilibrium with multiple GHR molecules. Nonetheless, the data suggest that the conformation of the GHR extracellular domain varies considerably, depending on whether it is in liquid phase (GHBP) or membrane-bound (native hGHR or chimeric hGHR/hG-CSFR). Models which use GHBP to characterize GH/GHR interactions should thus be interpreted with caution.

To ascertain whether these GH binding-induced conformational changes in the receptor are related to signalling, we examined whether or not hGH120R induces similar changes. As this mutant lacks hGH binding site 2, it cannot induce functional receptor dimerization and thus acts as an hGH antagonist (13, 16, 34). As also described for FDC-P1 cells transfected with a hybrid of the hGHR extracellular domain linked to the murine GM-CSFR transmembrane and intracellular domains (16), hGH120R cannot induce Ba/F3 (8/6) or IM9 cell proliferation (34, 36). This was originally attributed to non-formation of the "active" hGH-(GHR)$_2$ complex, but recent data show that hGHG120R dimerizes and interns the GHR as well as does GH (37). GHR05 binding does not increase in Ba/F3 (8/6) cells incubated with hGH120R, in contrast to its behavior with native hGH. Thus, the increased binding of this mAb is due to receptor epitope exposure upon dimerization with hGH, and GHR05 indeed recognizes an active GHR conformation necessary for signalling in response to growth hormone. Hence, hGHR conformation differs depending on whether it is complexed with hGH or with hGHG120R, and this alteration is sufficient to justify the signaling differences observed between these two ligands. GHR05 proves to be an extremely useful instrument for discrimination and characterization of the activated receptor form.

As GHR05 recognizes the active hGHR conformation and the epitope recognized is conformation-sensitive and important for signal transduction, we tested whether GHR05 acts on signalling through the receptor in the absence of hGH. We used an hGH-dependent transfected cell line which proliferates in the presence of hGH or when GHR05-treated. The GHR05-induced proliferation ratio correlates with the proportion of cells expressing the active epitope recognized by the antibody. hGH and GHR05 binding to the hGHR correlate with the expression of genes controlling cell survival and cell cycle, as both treatments induce signals leading to expression of bcl-2, a protein implicated in rescue from apoptosis. In addition, bax, p53 and c-myc, expressed during apoptosis, are detected when cells are treated with the irrelevant mAb, but not in the presence of hGH or GHR05. Thus, GHR05-promoted cell growth is a specific process triggered by specific binding of this mAb to the hinge between hGHR domain I and II, which is not the case for mAb which bind to other hGHR epitopes.

Although they are hGH-dependent, Ba/F3 (8/6) cells express a chimeric hGH receptor whose intracellular domain corresponds to that of the BG-CSF receptor. GHR05 also induces growth when cells expressing full-length hGHR, such as IM-9, are used. IM-9 cell growth is hGH-independent, although it responds to hGH by JAK2 tyrosine phosphorylation (36), immunoglobulin production and proliferation under certain experimental conditions (30). GHR05 also generates GH-specific signals in IM-9 cells, as it mimics the hGH-promoted activation of the JAK/STAT pathway.

Our results are compatible with a model in which the hGHR is transported to the membrane as a single chain that, upon expression on the cell surface, either aggregates or associates with other proteins. In such a complex, GHR05 recognition of the hinge region amino acid sequence between domains I and II is impeded. Upon binding to hGH, the hGHR undergoes transition to an active stage; this stage is distinguished by a modified conformation recognized by the antibody. This active conformation triggers a transduction pathway involving the phosphorylation of specific tyrosine motifs in the hGHR cytoplasmic domain, as well as the induction of specific transcriptional factors that lead to cell proliferation. Either a fraction of cells or a fraction of the hGHR in each cell is in the active conformation and thus subject to antibody recognition. These differential conformational or domain accessibility changes may be relevant in the physical recognition and association of the hGHR intracytoplasmic domain with JAK tyrosine kinases or in its interaction with the appropriate STATs. The characterization of this "active" state might therefore be germane for a clearer understanding of growth hormone-triggered signalling pathways.

FIGURE LEGENDS

FIG. 1. Principal characteristics of the GHR05 mAb. A, overlay of six sensorgrams showing hGHBP binding by GHR05. hGHBP concentrations (ranging from 4–500 nM) in a volume of 30 μl were passed sequentially over the flow cell and association monitored as resonance units (RU) on the sensorgram. After hGHBP injection, buffer flow was continued and dissociation measured. The histogram represents assay time in seconds (x axis) versus the relative response in RU (y axis). Arrows indicate the injection of GHR05 mAb (1) hGHBP (2) and buffer (3). A similar figure was obtained substituting hGH/hGHBP complex for hGHBP. B, values of hGHBP or hGH-hGHBP complex concentration (x axis) versus the association constant value ($K_s$) for each condition (y axis). The regression slope corresponds to the true association constant; a similar calculation was performed for the dissociation constant. C, recognition of glycosylated or non-glycosylalte hGHBP by GHR05 in a sandwich EIA using mAb 263 as capture antibody. The plot represents the hGHBP source (x axis) versus the OD$_{492}$ nm obtained by GHR05 as a percentage of the maximum signal (y axis). Data represent means of triplicate determinations, with the SD indicated.

FIG. 2. GHR05 binding to different hGHR-expressing cell lines. Ba/F3, Ba/F3 (8/6) and IM-9 cells in exponential growth were stained with GHR05. Histograms show GHR05 staining (x axis, continuous line) versus cell number (y axis), compared with an irrelevant isotype-matched mAb (dotted line).

Figure 3:
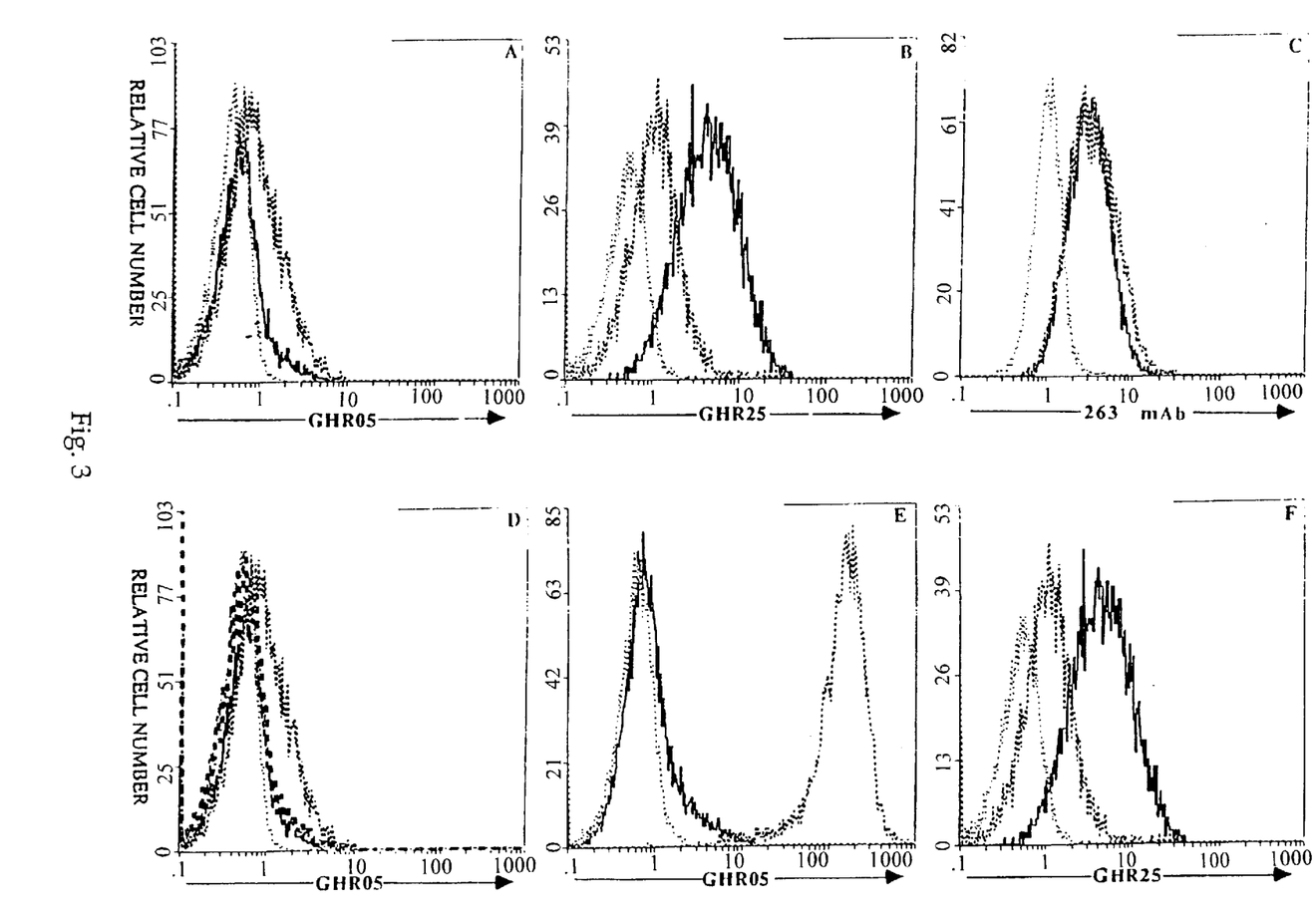
FIGS. 3A–F Effect of hGH, hGHG120R or permeabilization on anti-GHR mAb binding to Ba/F3 (8/6).
Figure 4:
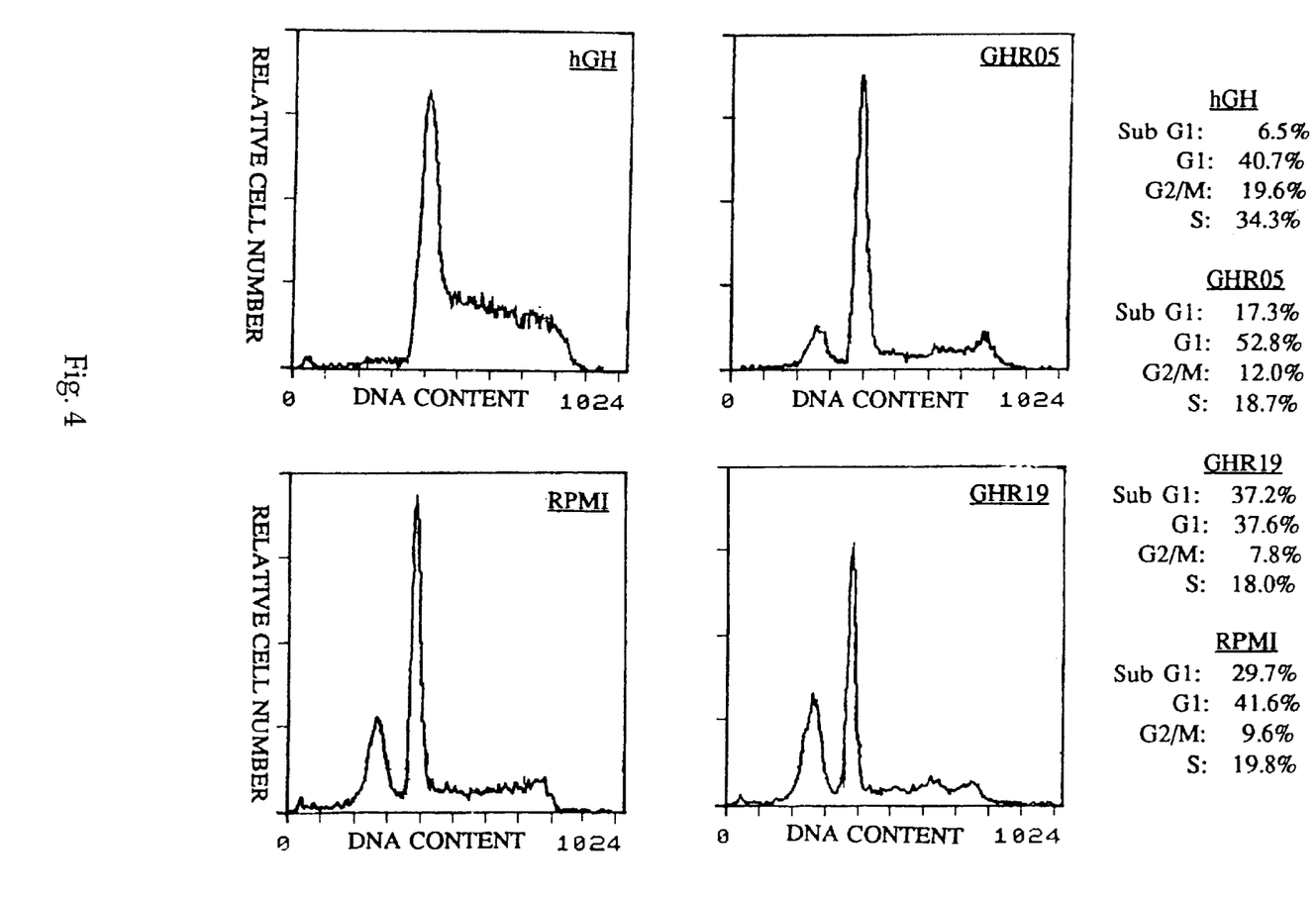
FIG. 4. Effect of hGH and GHR05 on cell cycle distribution of Ba/F3 (8/6) cells.

FIG. 3. Effect of hGH, hGHG120R or permeabilization on anti-GHR mAb binding to Ba/F3 (8/6). Ba/F3 (8/6) cells in exponential growth were stained with GHR05 (A, D & E), GHR25 (B & F) or 263 mAb (C). The upper panels show the effect of preincubation with hGH (10 μg/ml) (-----) on mAb binding (A, B & C). Panel D shows the effect of preincubation with hGHG120R (- - - -) or hGH (-----) on GHR05 binding. Panels E & F show the effect of permeabilization with ethanol (-----) on anti-GHR mAb binding compared with that in intact cells (____). Histograms show anti-GHR mAb staining (x axis) versus cell number (y axis). In each panel, dotted lines represent the staining of an irrelevant, isotype-matched mAb.

FIG. 4. Effect of hGH and GHR05 on cell cycle distribution of Ba/F3 (8/6) cells. Ba/F3 (8/6) cells were exposed to the indicated stimuli for 24 h in basal medium without hGH or IL-3, and cell cycle distribution determined by propidium iodide staining and flow cytofluorometry. Quiescent cells were cultured in exponential growth conditions in 10 μg/ml of hGH, 1 μg/ml of GHR05 or 1 μg/ml of the isotype-matched control mAb GHR19. Histograms show relative DNA content (x axis) versus cell number (y axis). Insets indicate the percentage of cells in each phase of the cell cycle.

FIG. 5. Expression of genes implicated in cell survival or death in hGH- or GHR05-treated Ba/F3 (8/6) cells. Cytokine-deprived Ba/F3 (8/6) cells were incubated for 20 h at 37° C. with hGH (10 μg/ml, lane 1), GHR05 (1 μg/ml, lane 2) or GHR19 (isotype-matched control mAb, 1 μg/ml, lane 3). The figure shows total lysates from $10 \times 10^6$ cells electrophoresed, transferred and immunoblotted with A, anti-mouse bcl-2 mAb, B, anti-mouse p53 mAb, C, anti-mouse c-myc mAb, and D, anti-mouse bax mAb.

Figure 6:
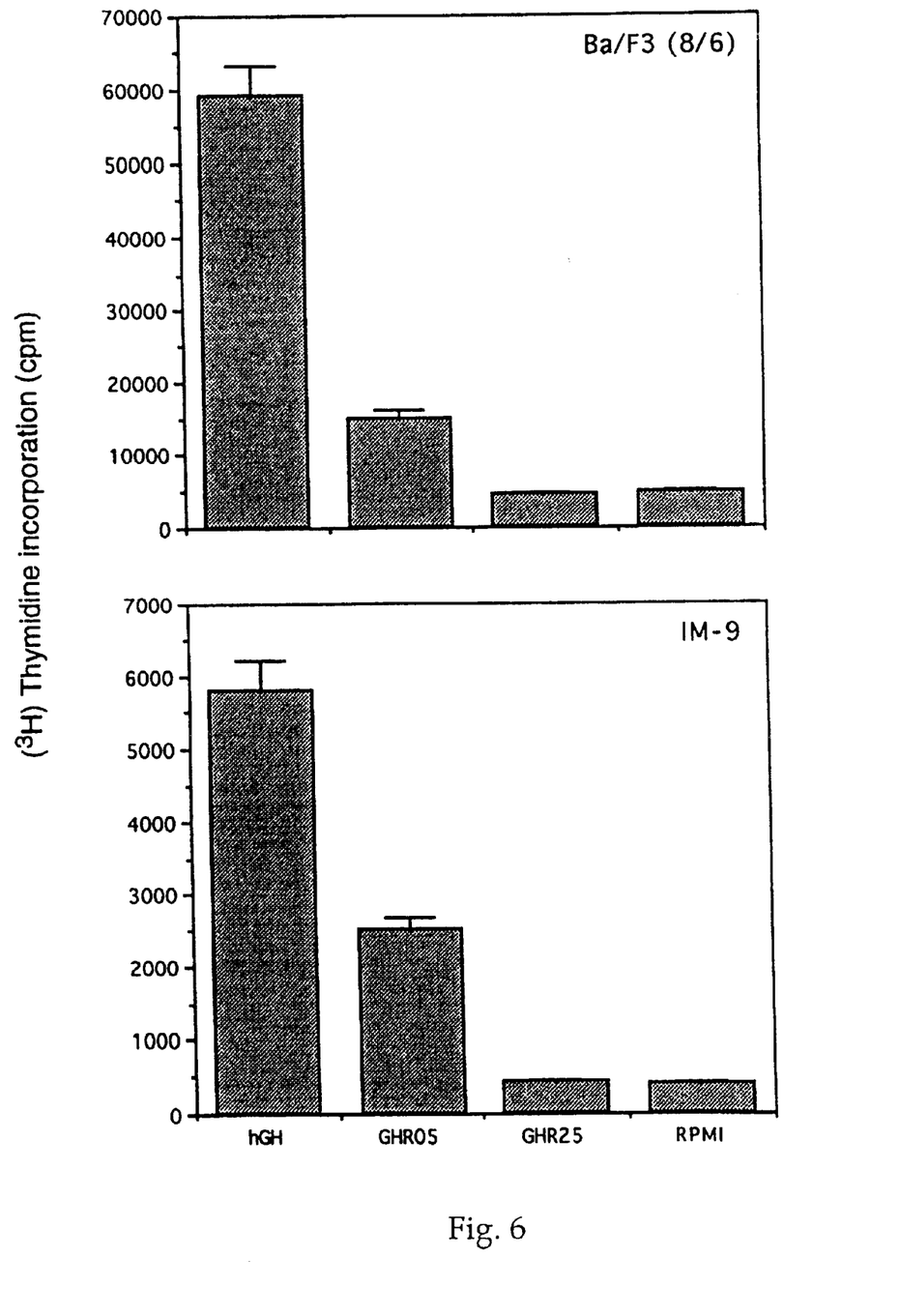
FIG. 6. Eat of GHR05 mAb on Ba/F3 (8/6) and IM-9 cell proliferation.
Figure 7:
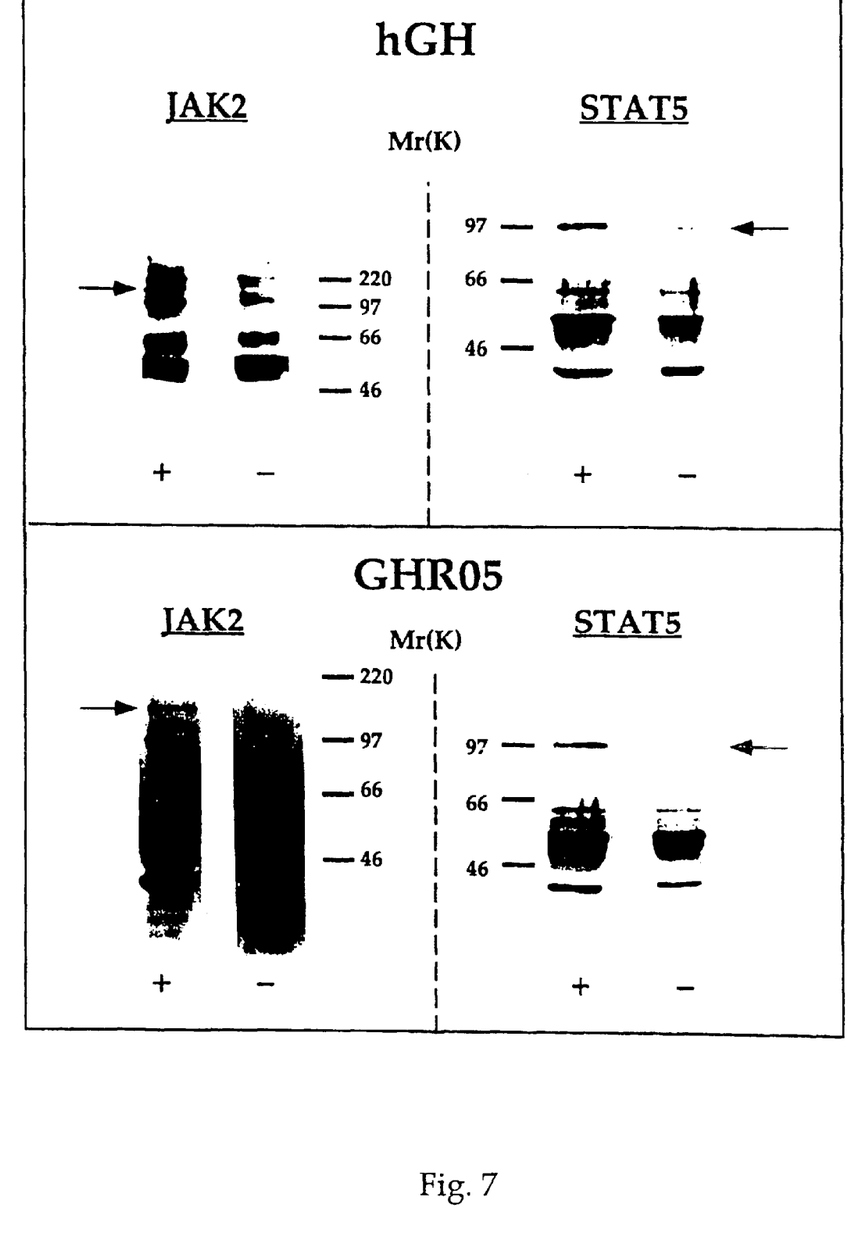
FIG. 7. Activation of JAK2 and STAT5 in hGH- or GHR05-treated IM-9 cells.

FIG. 6. Effect of GHR05 mAb on Ba/F3 (8/6) and IM-9 cell proliferation. Upper panel, Proliferation of Ba/F3 (8/6) cells in the presence of hGH (500 nM) or GHR05 (1 μg/ml) was determined by [$^3$H]thymidine incorporation into DNA. Cells cultured in the absence of cytokines were incubated for 20 h at 37° C. in flat-bottomed 96-well plates with hGH, GHR05, or GHR25 as control. [$^3$H]thymidine was added for 6 h, and cells harvested on glass-fiber filters. Lower panel, Proliferation of IM-9 cells in the presence of hGH (500 nM) or GHR05 (100 ng/ml) was determined after 8 h at 37° C. by [$^3$H]thymidine incorporation as above. Results of three experiments performed in quadruplicate are presented and SD are indicated. Histograms show cell treatment (x axis) versus [$^3$H]thymidine incorporation in cpm (y axis).

FIG. 7. Activation of JAK2 and STAT5 in hGH- or GHR05-treated IM-9 cells. Serum-deprived IM-9 cells were incubated for 5 min at 37° C. with hGH (500 nM, upper panel) or GHR05 (100 ng/ml, lower panel). The figure shows phosphotyrosine immunoprecipitates from $10 \times 10^6$ cells (+, cells treated for 5 min; −, untreated cells), immunoblotted with anti-human JAK2 mAb (left) or anti-human STAT5 mAb (right).

REFERENCES

1. Milman A. E. and Russell J. A. (1950) *Endocrinology* 47, 114–119
2. Swislocki N. L., Sonenberg M. and Yamasaki X (1970) *Endocrinology* 87, 900–904
3. Morikawa M., Nixon T. and Green H. (1982) *Cell* 29, 783–789
4. Okada S., Chen W. Y., Wiehl P., Kelder B., Goodman H. M., Guller S., Sonenberg M., and Kopchick J. J. (1992) *Endocrinology* 130, 2284–2290
5. Cosman D., Lyman S. D., Idzerda R. L., Beckmann M. P., Park S. L., Goodwin R. G. and March C. J. (1990) *Trends Biochem Sci.* 15, 265–270
6. Kelly P. A., Djiane J., Postel-Vinay M. and Edery M. (1991) *Endocrine reviews* 12, 235–251
7. Bazan J. F. (1989) *Biochem. Biophys. Res. Commun.* 164, 788–795
8. Thoreau E., Petridou B. Kelly P. A., Djiane J. and Momon J. P. (1991) *FEBS Lett.* 282, 26–31
9. Miyajima A, Kitamura T., Harada N., Yokota T., and Arai K. (1992) *Annu. Rev. Immunol.* 10, 295–331
10. Kitamura T., Ogorochi T and Miyajima A (1994) *Trends Endocrinol. Metab.* 5, 8–14
11. Leung D W, Spencer S. A., Cachianes G., Hammonds R. G., Collins C., Henzel W. J. Bamard R., Waters M. J. and Wood W. I. (1987) *Nature* 330, 537–543
12. Spencer S. A., Hammonds R. G., Henzel W. J., Rodriguez H., Waters M. J. and Wood W. I. (1988) *J. Biol. Chem.* 262, 7862–7867
13. Fuh G., Mulkerrin M. G., Bass S., McEarland N., Brochier M., Bourell J. H., Light D. R. and Wells J. A. (1989) *J. Biol. Chem.* 265, 3111–3115
14. Wells J. A. Binding in the growth hormone receptor complex (1996) *Proc. Natl. Aca. Sci. USA* 3, 1–6
15. de Vos A. M., Ultsch M. and Kossiakoff A. A. (1992) *Science* 255, 306–312
16. Fuh G., Cunningham B. C., Fukunaga R, Nagata S., Goeddel D. V. and Wells J. A. (1991) *Science* 256, 1677–1680
17. Argetsinger, L. S., Campbell G. S. Yang X., Witthuhn B. A., Silvennoinen O., Ihle J. N. and Carter-Su C. (1993) *Cell* 74, 237–244
18. Meyer D. J., Campbell G. S. Cochran B. H., Argetsinger L. S., Larner A. C., Finbloom D. S., Carter-Su C. and Schwartz J. (1994) *J. Biol. Chem.* 269, 4701–4704
19. Gronowski A. M. and Rotwein P. (1994). *J. Biol. Chem.* 269, 7874–7878
20. Hansen L. H., Wang X., Kopchick J. J., Bouchelouche P., Nielsen J. H., Galsgaard E. D. and Billestrup N. (1996) *J. Biol. Chem.* 271, 12669–12673
21. Xu B. C., Wang X., Darus C. J. and Kopchick J. J. (1996) *J. Biol. Chem.* 271, 19768–19773
22. Palacios R and Steinmetz M. (1985) *Cell* 41, 727–734
23. Galfre G., Howe S. C., Milstein C., Butcher G. W. and Howard J. C. (1977) *Nature* 266, 550–552
24. Harlow E. and Lane D., eds. (1988) *Antibodies: a laboratory manual.* Cold Spring Harbor, Cold Spring Harbor, N.Y.
25. Hoogenraad N. J. and Wraight C. J. (1986) *Methods Enzymol.* 121, 375–381
26. Fraker P. J. and Speck J. C. (1978) *Biochem. Biophys. Res. Commun.* 80, 849–857
27. Carrera A. C., Borlado L. R., Martínez-A C. and Mérida I. (1994) *J. Biol. Chem.* 269, 19435–19440
28. Lesniak M. A., Gorden P., Roth J. and Gavin J. R. III (1974) *J. Biol. Chem.* 249, 1661–1667
29. Suzuki K., Suzuki S., Saito Y, Ikebucbi H. and Terao T. (1990) *J. Biol. Chem.* 265, 11320–11327
30. Yoshida A, Ishioka C., Kimata H. and Mikawa H. (1992) *Acta Endocrinol.* 126, 524–529
31. Ilondo M. M., De Meyts P. and Bouchelouche P. (1994) *Biochem. Biophys. Res. Commun.* 202, 391–397
32. Mellado M., Rodriguez-Frade J. M., Kremer L., and Martinez-A C. (1996) *J. Clin. Endocrinol Metab.* 81, 1613–1618

33. Rowlinson S. W., Barnard R., Bastiras S., Robins A. J., Brinkworth R., and Waters M. J. (1995) *J. Biol. Chem.* 270, 16833–16839
34. Chen W. Y., Chen N., Yun J., Wagner T. E., and Kopchick J. J. (1994) *J. Biol. Chem.* 269, 15892–15897
35. Genaro A. M., Gonzalo J. A., Bosca L. and Martinez-A C. (1994) *Eur. J. Immunol.* 24, 2515–2521
36. Silva C. M., Lu H., Weber M. J. and Thorner M. O. (1994) *J. Biol. Chem.* 269, 27532–27539
37. Harding P. A., Xinzhong W., Okada S., Chen W. Y., Wan W., and Kopchick J. J. (1996) *J. Biol. Chem.* 271, 6708–6712

Samples of the monoclonal cell line expressing antibody GHR05 were deposited Under the Budapest Treaty at the DSMZ-Deutsche Sammlung Von Mikroorganismen Und Zellkulturen GmbH, Mascheroder Weg 1b, 38124 Braunschweig, Germany, on Dec. 19, 2000, under Accession Number: DSM ACC2486.

What is claimed is:

1. Method for determining growth hormone receptor activation by the use of GHR05 antibody, wherein the GHR05 antibody binds with a higher affinity to the active conformation of growth hormone receptor than it does to the inactive conformation of growth hormone receptor, the method comprising the steps of:
   (a) contacting the GHR05 antibody and the receptor to form a GHR05-receptor complex;
   (b) measuring the amount of the GHR05 antibody bound to the GHR05-receptor complex;
   (c) contacting a ligand to the GHR05-receptor complex to form a ligand-GHR05-receptor complex;
   (d) measuring the amount of the GHR05 antibody bound to the ligand-GHR05-receptor complex; and
   (e) comparing the amount of the GHR05 antibody bound in the presence of ligand to the amount of the GHR05 antibody bound in the absence of ligand, wherein growth hormone receptor activation is determined by an increase in the amount of the GHR05 antibody bound in the presence of ligand.

2. Method according to claim 1, wherein the ligand comprises growth hormone receptor agonist.

3. Method according to claim 2, wherein the growth hormone receptor agonist comprises human growth hormone receptor agonist.

4. Method according to claim 3, wherein the receptor in step (a) is inactive.

5. Method according to claim 4, wherein the inactive receptor comprises inactive human growth hormone receptor.

6. Method according to claim 1, wherein the receptor comprises human growth hormone binding protein.

7. Method according to claim 1, wherein the receptor comprises human growth hormone receptor.

8. Method according to claim 1, wherein the ligand comprises growth hormone.

9. Method according to claim 8, wherein the growth hormone comprises human growth hormone.

10. Method for determining growth hormone receptor activation by the use of GHR05 antibody, wherein the GHR05 antibody dissociates more slowly from the active conformation of a grow hormone receptor than it does from the inactive conformation of a growth hormone receptor, the method comprising the steps of:
    (a) contacting the GHR05 antibody and the receptor to form a GHR05-receptor complex;
    (b) measuring the rate at which the GHR05 antibody dissociates from the GHR05-receptor complex;
    (c) contacting a ligand to the GHR05-receptor complex to form a ligand-GHR05-receptor complex;
    (d) measuring the rate at which the GHR05 antibody dissociates from the ligand-GHR05-receptor complex; and
    (e) comparing the dissociation rate of the GHR05 antibody in the presence of ligand to the dissociation rate of the GHR05 in the absence of ligand, wherein growth hormone receptor activation is determined by a decrease in the dissociation rate of the GHR05 antibody in the presence of ligand.

11. Method according to claim 10, wherein the antibody is a Fab peptide derived from GHR05, or a single chain antibody derived from GHR05.

12. Method according to claim 10, wherein the ligand comprises growth hormone.

13. Method according to claim 12, wherein the growth hormone comprises human growth hormone.

14. Method according to claim 10, wherein the ligand comprises growth hormone receptor agonist.

15. Method according to claim 14, wherein the growth hormone receptor agonist comprises human growth hormone receptor agonist.

16. Method according to claim 10, wherein the receptor comprises human growth hormone receptor.

17. Method according to claim 10, wherein the receptor in step (a) is inactive.

18. Method according to claim 17, wherein the inactive receptor comprises inactive human growth hormone receptor.

19. Method according to claim 10, wherein the receptor comprises human growth hormone binding protein.

20. The monoclonal antibody GHR05.

* * * * *